United States Patent
Kowalik et al.

(12)

(10) Patent No.: US 6,464,996 B1
(45) Date of Patent: Oct. 15, 2002

(54) THICKENED ORGANIC FLUID/ SURFACTANT COMPOSITIONS AND USE THEREOF IN PESTICIDAL COMPOSITIONS

(75) Inventors: Ralph Martin Kowalik, Kingwood, TX (US); Karen K. Kuo, Seabrook, TX (US); Kishore K. Chokshi, Houston, TX (US); Paul Douglas Frisch, Kingwood, TX (US); R. Scott Tann, Sugar Land, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/860,136

(22) Filed: May 17, 2001

(51) Int. Cl.⁷ .................. A01N 25/00; A01N 25/08; A01N 37/18
(52) U.S. Cl. .............. 424/405; 424/409; 514/613; 514/622
(58) Field of Search ................. 424/405, 320, 424/409; 514/613, 622

(56) References Cited

U.S. PATENT DOCUMENTS

| 3,634,050 A |   | 1/1972 | Corino et al. |
| 4,195,096 A | * | 3/1980 | Graham et al. ............. 424/320 |
| 5,389,279 A | * | 2/1995 | Van Yu et al. ............. 252/108 |

FOREIGN PATENT DOCUMENTS

JP      07258689     * 12/1997

OTHER PUBLICATIONS

Melzer et al.Prog. Colloid Polym. Sci. (1997), 105 (Trends in Colloid and Interface Science XI), pp. 130–137.*

* cited by examiner

Primary Examiner—Russell Travers
Assistant Examiner—S. Jiang

(57) ABSTRACT

Disclosed are novel thickened organic fluid/surfactant compositions that are uniform, flowable and dispersible in water. Also disclosed are novel pesticidal compositions comprising a pesticide and the novel thickened organic fluid/surfactant composition.

12 Claims, No Drawings

THICKENED ORGANIC FLUID/ SURFACTANT COMPOSITIONS AND USE THEREOF IN PESTICIDAL COMPOSITIONS

FIELD OF THE INVENTION

This invention relates to compositions comprising an organic fluid, a surfactant and a thickening agent. The compositions are useful in many applications, particularly as a thickened oil flowable concentrate in which a pesticide may be incorporated.

BACKGROUND OF THE INVENTION

There is a need to package pesticides in non-aqueous concentrates that can be diluted and dispersed to sprayable application concentrations in water. As conventionally understood, the term, pesticide, is inclusive of insecticides, herbicides, fungicides, and other active ingredients. When the pesticide active ingredient is soluble in, for example, a hydrocarbon fluid, an emulsifiable concentrate solution can be made by combining suitable surfactants with the hydrocarbon fluid and active ingredient. When the active ingredient is not soluble in an organic fluid and not chemically stable in water, an alternative approach is needed.

One approach is to suspend pesticide particles in an organic fluid/surfactant solution. For the particles to remain suspended and not settle to the bottoms of their containers, the solution viscosity, before pesticide particles are added, generally must be about 1000 cP. This could be achieved with viscous hydrocarbon oils; however, most viscous hydrocarbon oils are phytotoxic. Consequently, one would prefer to use lower viscosity organic fluids that are not phytotoxic and to then thicken or viscosify the fluids to a suitable viscosity with a thickening agent. Common thickening agents for organic fluids that could be used include soluble polymers and network or structure forming compounds such as fumed silicas, clays, and materials that are crystalline or semi-crystalline in the fluid at application temperature, but soluble in the fluid at an elevated temperature.

While all these agents can thicken organic fluids, many are not compatible with the surfactants needed to disperse the concentrate in water. For example, a small concentration (about 5 wt %) of a high molecular weight (about 2 million) polyisobutylene can thicken a mixed aliphatic hydrocarbon. When a blend of surfactants that is soluble in the aliphatic hydrocarbon and capable of dispersing it in water is added, the complete mixture does not form a solution, but instead separates into two phases. Such two-phase mixtures are not suitable for the present application. A similar amount of a hydrophobic fumed silica can also thicken a mixed aliphatic hydrocarbon; however, when the same dispersing surfactant blend is added, the viscosity of the solution drops back close to the level of the neat hydrocarbon fluid, and the mixture is not suitable for the present application.

Another approach is to use small molecule thickening agents that build intermolecular networks and viscosity via, for example, hydrogen bonding. One such system, described in U.S. Pat. No. 3,634,050, uses the reaction product of gamma-butyrolactone and cocoalkylamine to gel hydrocarbon fluids. This system can accommodate the addition of surfactants needed to disperse the fluid in water, but it has a sharp transition from a low viscosity liquid to a gelled semi-solid as the concentration in the hydrocarbon fluid is increased. Consequently, it, too, is an unsuitable thickening agent for the present application.

It is an objective of the present invention to provide a composition comprising an organic fluid, a surfactant and a thickening agent, which composition is flowable, uniform, has sufficient viscosity to stabilize a pesticide when incorporated therein, and is dispersible in water.

It is a further objective of the present invention to provide compositions comprising a pesticide and a thickened organic fluid/surfactant composition as described herein.

These and other objects and advantages of the present invention will be apparent to those skilled in the art from the following detailed description and claims.

SUMMARY OF THE INVENTION

In accordance with this invention, it has been found that the above and still further objects are achieved by providing a composition comprising at least one, or more, organic fluids, at least one, or more, surfactants, and as a thickening agent a compound having the formula where R is a linear or branched alkyl group having about 2 to about 6 carbon atoms, preferably 3 to 5 carbon atoms, or mixtures thereof; and where X is a mixture of linear or branched alkyl or alkyl ether groups each having about 6 to about 21 carbon atoms, and from about 25 wt % to about 75 wt %, preferably 50 wt %, of the X groups have an average carbon number that is at least 4, preferably 6, more than the average carbon number of the other X groups.

The composition is uniform, flowable, and dispersible in water and has a viscosity that is from about 10 to about 1000 times larger than the viscosity of a corresponding composition having the same amounts of organic fluid and surfactant, but containing no thickening agent.

In accordance with this invention, it has been further found that there are provided useful pesticidal compositions comprising a pesticide and the thickened composition described herein, which thickened composition is uniform, flowable, dispersible in water, and has a viscosity that is from about 10 to about 1000 times larger than the viscosity of a corresponding composition having the same amounts of organic fluids and surfactants, but containing no thickening agent, and comprises at least one organic fluid, at least one surfactant, and as a thickening agent a compound having the formula where R is a linear or branched alkyl group having about 2 to about 6 carbon atoms, preferably 3 to 5 carbon atoms, or mixtures thereof; and where X is a mixture of linear or branched alkyl or alkyl ether groups each having about 6 to about 21 carbon atoms, and from about 25 wt % to about 75 wt %, preferably 50 wt %, of the X groups have an average carbon number that is at least 4, preferably 6, more than the average carbon number of the other X groups.

DETAILED DESCRIPTION OF THE INVENTION

The thickened organic fluid/surfactant compositions and the pesticidal compositions of the present invention are described in further detail as follows.

The thickened organic fluid/surfactant composition comprises:

(a) from about 82 to about 94 weight % of at least one, or more, organic fluid, (b) from about 5 to about 15 weight % of at least one, or more, surfactant that is soluble in the organic fluid and is capable of dispersing the organic fluid in water, and (c) from about 1 to about 3 weight %, as a thickening agent, of a compound having the formula

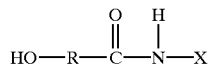

where R is a linear or branched alkyl group having about 2 to about 6 carbon atoms, preferably 3 to 5 carbon atom, or mixtures thereof; and where X is a mixture of linear or branched alkyl or alkyl ether groups each having about 6 to about 21 carbon atoms, and from about 25 wt % to about 75 wt %, preferably 50 wt %, of the X groups have an average carbon number that is at least 4, preferably at least 6, more than the average carbon number of the other X groups.

The composition is uniform, flowable, and dispersible in water and has a viscosity that is from about 10 to about 1000 times larger than the viscosity of a corresponding composition having the same amounts of organic fluid and surfactant, but containing no thickening agent.

Suitable organic fluids for use in the thickened compositions herein include, but are not limited to, aromatic and aliphatic hydrocarbons, alkyl esters, aromatic esters, glycol ethers, and mixtures thereof. Preferred fluids have flash points above 61° C., and most preferred fluids have flash points above 93° C. Neat fluid viscosities should also be below about 20 cP at 25° C. Examples of preferred fluids include Exxsol® D110 Fluid, Exxate® 1000 Fluid, Isopar® M Fluid, Norpar® 13 Fluid, Norpar® 14 Fluid, and Aromatic Fluid, all available from ExxonMobil Chemical Company.

Suitable surfactants for use in the thickened compositions herein include, but are not limited to, alkanolamides, alkylarylsulfonates, alkoxylated alcohols, alkoxylated alkylphenols, alkoxylated amines, alkoxylated amides, alkoxylated fatty acids, glycerol esters, phosphate esters, quaternary surfactants, soaps, sorbitan derivatives, sulfates of alcohols, sulfates of alkoxylated alcohols, sulfonates of dodecyl and tridecylbenzenes, sulfosuccinates and derivatives, and other amphiphilic compounds that can be found in, for example, McCutcheon's Volume 1: Emulsifiers & Detergents, 1997 North American Edition. Mixtures of the surfactants may be utilized.

The compound to be utilized as a thickening agent in the compositions herein may be prepared in any conventional manner. In a preferred embodiment, the compound is produced by reacting a lactone with an amine. More preferably, the thickening agent is produced by reacting at least one, or more, lactone, with at least two different primary alkyl or alkylether amines. In another preferred embodiment, the thickening agent may be the product of the reaction of at least two lactones with at least two different primary alkyl or alkylether amines. In a still further preferred embodiment, the thickening agent is produced by reacting together gamma-butyrolactone, epsilon-caprolactone, cocoalkylamine and hydrogenated tallowalkylamine.

Suitable amines for use herein include, but are not limited to, dodecylamine, hexadecylamine octadecylamine, oleylamine, cocoalkylamine, soyaalkylamine, tallowalkylamine, hydrogenated tallowalkylamine, isopropyloxypropylamine, isohexyloxypropylamine, 2-ethylhexyloxypropylamine, octyloxypropylamine, decyloxypropylamine, isodecyloxypropylamine, dodecyloxypropylamine, isododecyloxypropylamine, isotridecyloxypropylamine, tetradecyloxypropylamine, hexadecyloxypropylamine, octadecyloxypropylamine, and mixtures thereof.

Suitable lactones for use herein include, but are not limited to, beta-propiolactone, gamma-butyrolactone, gamma-valerolactone, epsilon-caprolactone, gamma-caprolactone, delta-valerolactone, and mixtures thereof.

An exemplary method for preparing the thickening agent used herein is as follows. The amine and lactone components are combined in a non-polar fluid at concentrations equal to or higher than the desired final concentrations thereof. The components are mixed well, with continuous agitation, to ensure complete reaction.

In a still further preferred embodiment of the present invention, the compound used as the thickening agent in the organic fluid composition herein has the formula

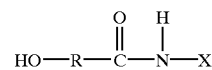

where R is a mixture of $C_4$ and $C_6$ alkyl groups, and from about 25 wt % to about 75 wt %, preferably about 50 wt %, of the groups are $C_4$ groups.

In a most preferred embodiment of the present invention, the thickened composition comprises:

(a) from about 82 to about 94 wt % of a substantially dearomatized (less than 1% aromatic compounds) mixed aliphatic hydrocarbon fluid having a boiling range of from about 200° C. to about 300° C., (b) from about 9 to about 11 wt %, preferably about 10 wt %, of a surfactant that is a mixture of ethoxylated amines and monoylphenol ethoxylates, and (c) from about 2.1 to about 2.5, preferably about 2.3, wt % of a thickening agent that is the reaction product of gamma-butyrolactone, epsilon-caprolactone, cocoalkylamine and hydrogenated tallowalkylamine.

The pesticidal compositions of the present invention comprise a pesticide and a thickened composition as described herein, which thickened composition is uniform, flowable, dispersible in water and has a viscosity that is from about 10 to about 1000 times larger than the viscosity of a corresponding composition having the same amounts of organic fluid and surfactant, but containing no thickening agent, and comprises at least one, or more, organic fluid, at least one, or more, surfactant, and as a thickening agent, a compound having the formula

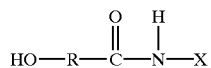

where R is a linear or branched alkyl group having about 2 to about 6 carbon atoms, preferably 3 to 5 carbon atoms, or mixtures thereof and where X is a mixture of linear or branched alkyl or alkyl ether groups each having about 6 to about 21 carbon atoms, and from 25 wt % to about 75 wt %, preferably 50 wt %, of the X groups have an average carbon number that is at least 4, preferably 6, more than the average carbon number of the other X groups.

The pesticidal composition may contain at least one, or more, pesticide suspended therein in an amount of from about 10 to about 80 wt %. Any pesticide may be utilized, and if desired, mixtures of pesticides may be utilized.

Examples of suitable pesticides include, but are not limited to, triazines like atrazine, simazine and propazine; sulfonylureas like nicosulfuron, tribenuron, and primisulfuron; carbamates like carbaryl and propoxur, imidazolinones like imazaquin and imazapyr; glyphosate and its carous salts; benzimidazoles like benomyl and thiabendazole; chlorothalonil; biologicals like various bacilli (*Bacillus thuringiensis, Bacillus sphaericus*) and spiosads; and strobilogens like azoxystrobin. This list is not meant to be exhaustive but to be representative of the types of pesticides that may be utilized herein.

Furthermore, it is desirable that the pesticide utilized has a melting point greater than 50° C., and a hardness appropriate for grinding and/or dispersing to fine particles. It is further desirable that the pesticide utilized has a solubility in the organic fluid that is low, typically less than 1%, and preferably even lower. Exemplary of these pesticides are acephate, sulfonylurea herbicides, chlorothalonil, dithiocarbamate fungicides and glyphosate.

In preparing the pesticidal compositions herein, there may be suitably utilized any of the organic fluids, surfactants and thickening agents described as being suitable in preparing the thickened compositions of the present invention.

With respect to the organic fluid used in preparing the pesticidal compositions of the present invention, it is preferred that the organic fluid not be reactive either in and of itself, or toward the pesticide. The low solvency aliphatic hydrocarbon fluids are most preferred. Exemplary are the dearomatized mixed aliphatics like Exxsol® D Fluids, isoparaffins like Isopar® Fluids and normal paraffins like Norpar® Fluids, all available from ExxonMobil Chemical Company.

If desired, other conventional additives may be incorporated into the thickened organic fluid/surfactant compositions and/or the pesticidal compositions of the present invention. In particular, other surfactants may be included to enhance the stability of the suspension of pesticide particles within the thickened organic fluid/surfactant composition.

The compositions of the present invention may be prepared by any method known in the art. In preparing the compositions of the examples herein, the components of the composition were added to a jar, raised to a temperature sufficient to melt all components, mixed well for about 15 minutes, and allowed to stand.

The invention will be more readily understood by reference to the following examples. There are, of course, many other forms of this invention which will become obvious to one skilled in the art and it will accordingly be recognized that these examples are given for the purpose of illustration only, and are not to be construed as limiting the scope of this invention in any way.

EXAMPLES

The following test procedures were used to evaluate the properties of the compositions herein.

Uniformity—The thickened organic fluid/surfactant composition has the same visual appearance and bulk properties throughout so that any structures within the composition occur on a scale that is too small to be visually discriminated by an unaided human eye. This uniform condition does not change via phase separation, settling, or floating for at least one month.

Flowability—The thickened organic fluid/surfactant composition can be poured out of a full one-gallon container through a two-inch diameter opening to empty 95% of the contents of the container in less than 10 minutes.

Viscosity—The viscosities of organic fluid/surfactant and thickened organic fluid/surfactant compositions are measured with a Brookfield LVTD Viscometer using a #2 cylindrical spindle inserted into 1.3 ounce vials that have an inside diameter of about 2 cm and are filled with about 25 ml of the liquid composition.

Dispersion in Water—A organic fluid/surfactant or thickened organic fluid/surfactant composition is dispersible in water when 2.5 grams of the material placed in a 6 inch by 1 in diameter test tube rapidly forms a uniform, turbid emulsion as 47.5 grams of water are added, in approximately 5 seconds, to the test tube from a 250 ml separatory funnel with its valve fully opened.

In each of the following examples, the surfactant was the same, and is identified as "Surfactant." Surfactant was a blend, prepared by combining the following four surfactants at the indicated weight percents.

| Surfactant | Weight % |
| --- | --- |
| Chemeen ® T-5 (ethoxylated (5) tallowalkylamine) | 30 |
| Ethomeen ® C/15 (ethoxylated (5) cocoalkylamine) | 20 |
| Igepal ® CO-430 (ethoxylated (4) nonylphenol) | 20 |
| Igepal ® CO-630 (ethoxylated (9) nonylphenol) | 30 |

*Chemeen ® is a registered trademark for surfactants available from Chemax.
*Ethomeen ® is a registered trademark for surfactants available from Akzo-Nobel.
*Igepal ® is a registered trademark for surfactants available from Rhodia.

Examples 1–5

Examples 1–5 are comparative runs. In each of Examples 1–5 the same thickening agent was used, but at increasing concentrations. The thickening agent utilized was prepared by combining 1.5 grams of gamma-butyrolactone, 1.76 grams of cocoalkylamine, and 2.27 grams of hydrogenated tallowalkylamine with 94.6 grams of Exxsol® D110 Fluid (mixed aliphatic hydrocarbon fluid available from Exxon-Mobil Chemical Company). The amines and Exxsol D110 Fluid were combined in an 8 ounce jar, mixed with a magnetic stirrer, and heated to about 60° C. to ensure melting and dissolution of the hydrogenated tallowalkylamine. The liquid lactone was then added to the solution. The combined materials were mixed with a magnetic stirrer and then kept at 60° C. for about 5 hours. They were then allowed to stand at room temperature. After about 1 week, the material was observed as being a transparent, solid gel that did not flow upon inverting the jar.

The gelled material thus formed was heated to a temperature of about 60–70° C., and combined with Surfactant, as previously described, and additional Exxsol® D110 Fluid, according to the weights in grams, as shown in the following Table 1. In all instances, the samples were prepared in 1.3 ounce vials, mixed on a vortex mixer, and allowed to stand at room temperature. The observations noted in Table 1 are after about 3 weeks.

TABLE 1

| Example No. | 1 | 2 | 3 | 4 | 5 |
|---|---|---|---|---|---|
| Gelled Material, grams | 1.11 | 2.03 | 3.08 | 4.06 | 5.14 |
| Surfactant, grams | 2.01 | 2.00 | 2.07 | 2.05 | 2.11 |
| Exxsol ® D110 Fluid, grams | 17.15 | 16.15 | 15.11 | 14.09 | 13.08 |
| Thickening agent, wt % | 0.30 | 0.56 | 0.84 | 1.11 | 1.40 |
| Surfactant, wt % | 9.92 | 9.91 | 10.22 | 10.15 | 10.38 |
| Exxsol ® D110 Fluid, wt % | 89.78 | 89.53 | 88.94 | 88.74 | 88.23 |
| Uniform | no | no | no | no | yes |
| Flowable | yes | yes | yes | yes | no |

From the above data, it is observed that none of the thickened organic fluid/surfactant compositions of Examples 1–5 was characterized as being both uniform and flowable.

Examples 6–14

Examples 6–14 are comparative runs. In each of Examples 6–14 the same thickening agent was used, but at increasing concentrations. The thickening agent utilized was prepared by combining 0.76 grams of gamma-butyrolactone, 1.08 grams of epsilon-caprolactone, 1.72 grams of cocoalkylamine, and 2.28 grams of hydrogenated tallowalkylamine with 94.2 grams of Exxsol® D110 Fluid (mixed aliphatic hydrocarbon fluid available from Exxon-Mobil Chemical Company). The amines and Exxsol® D110 Fluid were combined in an 8 ounce jar, mixed with a magnetic stirrer, and heated to about 60° C. to ensure melting and dissolution of the hydrogenated tallowalkylamine. The liquid lactones were then added to the solution. The combined materials were mixed with a magnetic stirrer and then kept at 60° C. for about 5 hours. They were then allowed to stand at room temperature. After about 1 week, the material was observed as being an opaque gel that flowed slowly upon inverting the jar.

The gelled material thus formed was heated to a temperature of about 60–70° C. to liquefy it and then combined with Surfactant, as previously described, and additional Exxsol®D110 Fluid according to the weights in grams, as shown in the following Table 2. In all instances, the samples were prepared in 1.3 ounce vials, mixed on a vortex mixer, and allowed to stand at room temperature. The observations noted in Table 2 are after about 2 weeks for Examples 6–12, and after about 1 week for Examples 13 and 14.

TABLE 2

| Example No. | 6 | 7 | 8 | 9 | 10 | 11 | 12 | 13 | 14 |
|---|---|---|---|---|---|---|---|---|---|
| Gelled Material, grams | 1.09 | 2.01 | 3.04 | 4.07 | 5.06 | 6.07 | 7.13 | 9.18 | 10.03 |
| Surfactant, grams | 2.05 | 2.01 | 2.03 | 2.17 | 2.06 | 2.02 | 2.02 | 2.02 | 2.01 |
| Exxsol ® D110 Fluid, grams | 17.05 | 16.03 | 15.07 | 14.09 | 13.05 | 12.06 | 11.06 | 9.06 | 8.04 |
| Thickening agent, wt % | 0.32 | 0.59 | 0.88 | 1.17 | 1.47 | 1.76 | 2.06 | 2.65 | 2.92 |
| Surfactant, wt % | 10.15 | 10.03 | 10.08 | 10.67 | 10.21 | 10.03 | 10.00 | 9.97 | 10.01 |
| Exxsol ® D110 Fluid, wt % | 89.53 | 89.39 | 89.04 | 88.16 | 88.32 | 88.22 | 87.95 | 87.38 | 87.07 |
| Uniform | no | no | No | no | no | no | no | yes | yes |
| Flowable | yes | yes | Yes | yes | yes | yes | yes | no | no |

From the above data, it is observed that none of the thickened organic fluid/surfactant compositions of Examples 6–14 was characterized as being both uniform and flowable.

Example 15

Example 15 is representative of the present invention. In this example, the thickening agent utilized was prepared by combining 0.76 grams of gamma-butyrolactone, 1.08 grams of epsilon-caprolactone, 1.72 grams of cocoalkylamine, and 2.28 grams of hydrogenated tallowalkylamine with 94.2 grams of Exxsol® D110 Fluid (mixed aliphatic hydrocarbon fluid available from ExxonMobil Chemical Company). The amines and Exxsol® D110 Fluid were combined in an 8 ounce jar, mixed with a magnetic stirrer, and heated to about 60° C. to ensure melting and dissolution of the hydrogenated tallowalkylamine. The liquid lactones were then added to the solution. The combined materials were mixed with a magnetic stirrer and then kept at 60° C. for about 5 hours. They were then allowed to stand at room temperature. After about 1 week, the material was observed as being an opaque gel that flowed slowly upon inverting the jar.

The gelled material thus formed was heated to a temperature of about 60–70° C. to liquefy it, and an amount of 8.05 grams of the liquefied material was combined with 2.06 grams of Surfactant, as previously described, and 10.05 grams of Exxsol® D110 Fluid in a 1.3 ounce vial. The ingredients were then mixed on a vortex mixer and allowed to stand at room temperature. The thickened composition comprised 2.33 weight % thickening agent, 10.22 weight % Surfactant, and 87.45 weight % Exxsol® D110 Fluid. After about 1 month, it was observed that the thickened organic fluid/surfactant composition was both uniform and flowable.

Example 16

For purpose of exemplification of viscosity and dispersion in water, a control sample was prepared as follows. 10 parts by weight of Surfactant previously described herein was combined with 90 parts by weight of Exxsol® D110 Fluid to provide a 10% surfactant solution. The viscosity of the surfactant solution was then compared with the viscosity of the sample of Example 15, as shown in the following Table 3. 2.5 grams of Examples 15 and 16 were also placed in test tubes to which 47.5 grams of water were added via a 250 ml separatory funnel. Both rapidly formed turbid, uniform emulsions showing them to be dispersible in water.

TABLE 3

| | Viscosity at Ambient Temperature, cP | |
|---|---|---|
| Spindle RPM | Example 15 | Example 16 (control) |
| 0.3 | 2000 | * |
| 0.6 | 1500 | * |
| 1.5 | 940 | * |
| 3 | 700 | 70 |
| 6 | 400 | 20 |
| 12 | 282 | 7.5 |
| 30 | 143 | 4 |
| 60 | 90 | 5 |

*Viscosities were too low for the range of the instrument.

The above data show that a compositions of the present invention containing a thickening agent has viscosities of from about 10 times larger than a similar composition without the thickening agent and are dispersible in water.

It should be clearly understood that the forms of the invention herein described are illustrative only and are not intended to limit the scope of the invention. The present invention includes all modifications falling within the scope of the following claims.

We claim:

1. A pesticidal composition which comprises a pesticide and a uniform, flowable, dispersible in water, composition comprising:
   (a) from about 82 to about 94 weight % of at least one organic fluid,
   (b) from about 5 to about 15 weight % of at least one surfactant that is soluble in the at least one organic fluid, and
   (c) from about 1 to about 3 weight %, as a thickening agent, of a mixture of compounds having the formula:

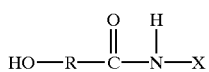

wherein R is a linear or branched alkyl group having from about 2 to about 6 carbon atoms,
   wherein X is a linear or branched alkyl or alkyl ether group having from about 6 to about 21 carbon atoms,
   wherein the mixture of compounds comprises at least two different X groups and from about 25 weight % to about 75 weight % of the X groups have an average carbon number that is at least 4 more than the average carbon number of the remaining X groups, and
   wherein the uniform, flowable, dispersible in water, composition has a viscosity of from about 10 to about 1000 times larger than the viscosity of a corresponding uniform, flowable, dispersible in water, composition comprising the same amounts of (a) and (b), in the absence of (c).

2. The pesticidal composition according to claim 1 wherein the R of the formula is a linear or branched alkyl group having from about 3 to about 5 carbon atoms and wherein about 50 weight % of the X groups have an average carbon number that is at least 6 more than the average carbon number of the remaining X groups.

3. The pesticidal composition of claim 1 wherein R of the formula is a linear or branched alkyl group having from about 4 to about 6 carbon atoms and from about 25 weight % to about 75 weight % of the groups have 4 carbon atoms.

4. The pesticidal composition according to claim 3 wherein about 50 weight % of the groups have 4 carbon atoms.

5. The pesticidal composition according to claim 1 wherein the compounds of the formula are a product of the reaction of at least one or more lactones with at least two different amines selected from the group consisting of primary alkyl amines and primary alkyl ether amines.

6. The pesticidal composition according to claim 1 wherein the compounds are a product of reaction of at least two lactones.

7. The pesticidal composition according to claim 6 wherein the lactones are gamma-butyrolactone and epsilon-caprolactone, and the amines are cocoalkylamine and hydrogenated tallowalkylamine.

8. The pesticidal composition according to claim 1 wherein the organic fluid is a mixed aliphatic hydrocarbon having less than 1% aromatic compounds and having a boiling range of from about 200° C. to about 300° C., the surfactant is a mixture of ethoxylated amines and nonylphenol ethoxylates present in an amount of from about 9 to about 11 weight %, and the compound is present in an amount of from 2.1 to about 2.5 weight %.

9. The pesticidal composition according to claim 8 wherein the surfactant is present in an amount of about 10 weight %, and the compound is present in an amount of about 2.3 weight %.

10. The pesticidal composition according to claim 1 wherein the pesticide is suspended in the uniform, flowable, dispersible in water, composition in an amount ranging from about 10 to about 80 weight %.

11. The pesticidal composition according to claim 8 wherein the pesticide is suspended in the uniform, flowable, dispersible in water, composition in an amount ranging from about 10 to about 80 weight %.

12. The pesticidal composition according to claim 9 wherein the pesticide is suspended in the uniform, flowable, dispersible in water, composition in an amount ranging from about 10 to about 80 weight %.

* * * * *